United States Patent
Hassan et al.

(10) Patent No.: US 8,729,290 B2
(45) Date of Patent: *May 20, 2014

(54) METHOD OF MAKING GLYCEROL

(75) Inventors: Abbas Hassan, Sugar Land, TX (US); Ebrahim Bagherzadeh, Sugar Land, TX (US); Rayford Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 35 days.

This patent is subject to a terminal disclaimer.

(21) Appl. No.: 13/584,219

(22) Filed: Aug. 13, 2012

(65) Prior Publication Data

US 2012/0302800 A1  Nov. 29, 2012

Related U.S. Application Data

(63) Continuation of application No. 12/144,440, filed on Jun. 23, 2008, now Pat. No. 8,502,000.

(60) Provisional application No. 60/946,482, filed on Jun. 27, 2007.

(51) Int. Cl.
 *C07C 261/00* (2006.01)
(52) U.S. Cl.
 USPC ........................................................ 560/24
(58) Field of Classification Search
 USPC ................................................ 568/852, 860
 See application file for complete search history.

(56) References Cited

U.S. PATENT DOCUMENTS

| | | | |
|---|---|---|---|
| 3,125,305 | A | 3/1964 | Willems |
| 3,887,167 | A | 6/1975 | Irwin |
| 3,954,815 | A | 5/1976 | Fisher et al. |
| 4,396,527 | A | 8/1983 | Matsuyama et al. |
| 4,842,765 | A * | 6/1989 | Satomi ................. 252/186.26 |
| 4,900,847 | A | 2/1990 | Hanson et al. |
| 5,110,443 | A * | 5/1992 | Gregoli et al. ................. 208/46 |
| 5,157,090 | A | 10/1992 | Wilhelm et al. |
| 5,538,191 | A | 7/1996 | Holl |
| 5,877,350 | A | 3/1999 | Langer et al. |
| 6,316,641 | B1 | 11/2001 | Yoo et al. |
| 6,368,366 | B1 | 4/2002 | Langer et al. |
| 6,368,367 | B1 | 4/2002 | Langer et al. |
| 6,383,237 | B1 | 5/2002 | Langer et al. |
| 6,530,964 | B2 | 3/2003 | Langer et al. |
| 6,742,774 | B2 | 6/2004 | Holl |
| 7,383,723 | B2 * | 6/2008 | Tregub et al. ................. 73/61.71 |
| 2003/0043690 | A1 | 3/2003 | Holl |
| 2004/0052158 | A1 | 3/2004 | Holl |
| 2004/0191667 | A1 | 9/2004 | Kurokawa |
| 2005/0033069 | A1 | 2/2005 | Holl et al. |
| 2005/0131179 | A1 * | 6/2005 | Cozens et al. .............. 526/230.5 |
| 2006/0245991 | A1 | 11/2006 | Holl et al. |
| 2008/0279928 | A1 | 11/2008 | Moschwitzer |

FOREIGN PATENT DOCUMENTS

WO  02064708 A2  8/2002

OTHER PUBLICATIONS

Mugdan, M. et al. "Catalytic hydroxylation of unsaturated compounds," J. Chem. Soc. (1949) 2988-3000.*
Mugdan et al. (Catalytic hydroxylation of unsaturated compounds, J. Chem. Soc., 2988-3000, 1949).*
Gogate et al., "Cavitation: A technology on the horizon," Current Science 91 (No. 1): 35-46 (2006).
IKA-Rotor-Stator Generators—2003 Processing Catalog; 38 pages.
International Search Report and Written Opinion dated Oct. 31, 2008 for corresponding International Patent Application No. PCT/US2008/068218; 10 pages.
Extended European Search Report dated Jul. 8, 2010 for corresponding European Patent Application No. 08780993.5; 8 pages.
Office Action dated Jun. 25, 2009 for U.S. Appl. No. 12/142,447.
Office Action dated Jan. 7, 2010 for U.S. Appl. No. 12/142,447.
Office Action dated May 13, 2010 for U.S. Appl. No. 12/142,447.
Office Action dated Feb. 4, 2010 for U.S. Appl. No. 12/492,721.
Office Action dated Feb. 18, 2010 for U.S. Appl. No. 12/635,433.
Office Action dated Feb. 18, 2010 for U.S. Appl. No. 12/635,454.
Office Action dated May 14, 2010 for U.S. Appl. No. 12/137,441.
Office Action dated Feb. 19, 2010 for U.S. Appl. No. 12/144,459.
Office Action dated Sep. 2, 2009 for U.S. Appl. No. 12/142,433.
Office Action dated Jan. 29, 2010 for U.S. Appl. No. 12/142,433.
Office Action dated May 24, 2010 for U.S. Appl. No. 12/142,433.
Office Action dated Apr. 30, 2010 for U.S. Appl. No. 12/141,191.
Office Action dated Oct. 27, 2009 for U.S. Appl. No. 12/142,120.
Office Action dated May 5, 2010 for U.S. Appl. No. 12/571,537.
Notice of Allowance dated Jul. 2, 2013 for corresponding U.S. Appl. No. 12/144,440 (8 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
Office Action dated Oct. 28, 2011 for U.S. Appl. No. 12/144,440 (8 pgs.).

(Continued)

*Primary Examiner* — Brandon Fetterolf
*Assistant Examiner* — Blaine G Doletski
(74) *Attorney, Agent, or Firm* — Timothy S. Westby; Porter Hedges LLP

(57) ABSTRACT

Method of producing glycerol that includes mixing a peroxide stream with an olefenic alcohol stream to form a feed stream; processing the feed stream in a high shear device to produce a high shear dispersion of peroxide and olefinic alcohol, wherein the high shear device is configured with a rotor and a stator separated by a shear gap; and contacting the high shear dispersion with a catalyst in a reactor to produce glycerol.

13 Claims, 2 Drawing Sheets

(56) References Cited

OTHER PUBLICATIONS

Office Action dated Dec. 20, 2012 for U.S. Appl. No. 12/144,440 (10 pgs.).

Milas et al., "The Hydroxylation of the Double Bond," JACS, vol. 58, dated Jul. 1936, pp. 1302-1304 (3 pgs.).

* cited by examiner

METHOD OF MAKING GLYCEROL

CROSS-REFERENCE TO RELATED APPLICATIONS

This application is a continuation application of U.S. patent application Ser. No. 12/144,440, filed Jun. 23, 2008 (now U.S. Pat. No. 8,502,000, issued Aug. 6, 2013), which application claims the benefit under 35 U.S.C. §119(e) of U.S. Provisional Patent Application No. 60/946,482, filed Jun. 27, 2007. The disclosure of each application is hereby incorporated herein by reference in entirety for all purposes.

STATEMENT REGARDING FEDERALLY SPONSORED RESEARCH OR DEVELOPMENT

Not Applicable.

TECHNICAL FIELD

The invention generally relates to apparatus and methods for making glycerol, and more particularly related to the acceleration of such reactions by high shear mixing.

BACKGROUND OF THE INVENTION

Glycerol is one of the simplest trihydric alcohols, with the formula $CH_2OHCHOHCH_2OH$. The name glycerol is preferred for the pure chemical, but the commercial product is usually called glycerin. It is widely distributed in nature in the form of its esters, called glycerides. The glycerides are the principal constituents of the class of natural products known as fats and oils.

Glycerin is used in nearly every industry. With dibasic acids, such as phthalic acid, it reacts to make the important class of products known as alkyl resins, which are widely used as coating and in paints. It is used in innumerable pharmaceutical and cosmetic preparations; it is an ingredient of many tinctures, elixirs, cough medicines, and anesthetics; and it is a basic medium for toothpaste. In foods, it is an important moistening agent for baked goods and is added to candies and icings to prevent crystallization. It is used as a solvent and carrier for extracts and flavoring agents and as a solvent for food colors. Many specialized lubrication problems have been solved by using glycerin or glycerin mixtures. Many millions of pounds are used each year to plasticize various materials.

There are several routes to synthetic glycerine. One route involves four process steps—the chlorination of propylene to allyl chloride, the chlorohydrination of allyl chloride to glycerol dichlorohydrins, the hydrolysis of the dichlorohydrins to epichlorohydrin, and the hydrolysis of epichlorohydrin to glycerine. A second route is based upon three process steps—the oxidation of propylene to acrolein, the hydroxylation of acrolein to allyl alcohol, and the hydroxylation of allyl alcohol to glycerine. The third route also employs three steps—the epoxidation of propylene to propylene oxide, isomerization of propylene oxide to allyl alcohol, and the hydroxylation of the allyl alcohol to glycerine. As can be seen from the above, much work has been done in altering the chemistry of the reactions while little investigation has been done with regard improving the mixing of the reactants to accelerate the reaction rate.

Consequently, there is a need for simple accelerated methods for making glycerol by improving the mixing of the olefinic alcohol and peroxide.

SUMMARY

Methods and systems for the hydroxylation of olefenic alcohols are described herein. The methods and systems incorporate the novel use of a high shear device to promote mixing and solubility of peroxides with the olefenic alcohol. The high shear device may allow for lower reaction temperatures and pressures and may also reduce hydroxylation time with existing catalysts. Further advantages and aspects of the disclosed methods and system are described below.

In an embodiment, a method of making glcyerol comprises introducing a peroxide into an olefenic alcohol stream to form a reactant stream. The method also comprises subjecting said reactant stream to a shear rate of greater than about 20,000 s$^{-1}$ with a high shear device. In addition, the method comprises contacting the reactant stream with a catalyst to hydroxylate the olefenic alcohol and make glycerol.

In an embodiment, a system for the making glycerol comprises at least one high shear device comprising a rotor and a stator. The rotor and the stator are separated by a shear gap in the range of from about 0.02 mm to about 5 mm. The shear gap is a minimum distance between the rotor and the stator. The high shear mixing device is capable of producing a tip speed of the at least one rotor of greater than about 23 m/s (4,500 ft/min). In addition, the system comprises a pump configured for delivering a liquid stream comprising liquid phase to the high shear mixing device. The system also comprises a reactor for hydroxylation of an olefenic alcohol coupled to the high shear device. The reactor is configured for receiving a liquid reactant stream from the high shear device.

Embodiments of the disclosure pertain to a method of producing glycerol that may include the steps of mixing a peroxide stream with an olefenic alcohol stream to form a feed stream; processing the feed stream in a high shear device to produce a high shear dispersion of peroxide and olefinic alcohol, wherein the high shear device may be configured with a rotor and a stator separated by a shear gap; and contacting the high shear dispersion with a catalyst in a reactor to produce glycerol.

In aspects, the high shear dispersion may include bubbles with an average bubble diameter of less than about 5 microns. Olefinic alcohol in the high shear dispersion may be hydroxylated to produce glycerol. In other aspects, wherein the peroxide stream may include hydrogen peroxide, ethylbenzyl hydroperoxide, t-butyl hydroperoxide, t-amyl hydroperoxide, cumene hydroperoxide, 2-methyl-2-hydroperoxy-methyl proprionate, 2-methyl-2-hydroperoxy propanoic acid, pyrrolehydroperoxide, furan hydroperoxide, 2-butylhydroperoxide, cyclohexyl hydroperoxide, and 1-phenyl-ethylhydroperoxide, or combination thereof.

In yet other aspects, the olefenic alcohol stream may include allyl alcohol, methallyl alcohol, cinnamyl alcohol, methyl vinyl carbinol, dimethyl allyl alcohol, oleyl alcohol, methyl vinyl carbinol, crotyl alcohol, methyallyl alcohol, cyclohexenol, or combinations thereof.

The high shear device may be operable at a tip speed of at least about 23 msec, and may produce a shear rate of greater than about 20,000 s$^{-1}$. In forming the dispersion the high shear device may have an energy expenditure of at least about 1000 W/m$^3$. In some aspects, the shear gap may be in the range of from about 0.02 mm to about 5 mm. In other aspects, the method may include introducing the high shear dispersion to a fixed bed containing additional catalyst. The catalyst may include a metal oxide, a tungstic catalyst, an osmium catalyst, formic acid, sulfonic acid, sulfuric acid, or combinations thereof. Each of the rotor and the stator may include a toothed surface.

Other embodiments of the disclosure pertain to a method of producing glycerol that may include mixing a peroxide stream with an olefenic alcohol stream to form a reactant stream; processing the reactant stream in a high shear device to produce a high shear dispersion comprising peroxide and olefinic alcohol; and contacting the high shear dispersion with a catalyst in a reactor to produce glycerol, wherein the reactor may be operable at a bulk reaction pressure of about 10 to about 60 atm, and a bulk reaction temperature of about 20° C. to about 80° C. In aspects, the high shear device may be configured with a rotor and a stator separated by a shear gap.

The high shear dispersion may include bubbles having an average bubble size less than about 1.5 μm. The high shear dispersion may include bubbles with an average diameter of less than about 5 microns. Olefinic alcohol in the high shear dispersion may be hydroxylated to produce glycerol.

In aspects, the peroxide stream may include hydrogen peroxide, ethylbenzyl hydroperoxide, t-butyl hydroperoxide, t-amyl hydroperoxide, cumene hydroperoxide, 2-methyl-2-hydroperoxy-methyl proprionate, 2-methyl-2-hydroperoxy propanoic acid, pyrrolehydroperoxide, furan hydroperoxide, 2-butylhydroperoxide, cyclohexyl hydroperoxide, and 1-phenyl-ethylhydroperoxide, or combination thereof. In other aspects, the olefenic alcohol stream may include allyl alcohol, methallyl alcohol, cinnamyl alcohol, methyl vinyl carbinol, dimethyl allyl alcohol, oleyl alcohol, methyl vinyl carbinol, crotyl alcohol, methyallyl alcohol, cyclohexenol, or combinations thereof.

The high shear device may be operable at a tip speed of at least about 23 msec. The high shear device may produce a shear rate of greater than about 20,000 s$^{-1}$. In forming the dispersion, the high shear device may operate with an energy expenditure of at least about 1000 W/m$^3$. The shear gap may be in the range of from about 0.02 mm to about 5 mm.

The catalyst may include a metal oxide, a tungstic catalyst, an osmium catalyst, formic acid, sulfonic acid, sulfuric acid, or combinations thereof.

In aspects, the high shear device may include at least two generators. In further aspects, the shear rate provided by one generator is greater than the shear rate provided by another generator.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION

The disclosed methods and systems for the production of glycerol employ a high shear mechanical device to provide rapid contact and mixing of peroxide and alcohol in a controlled environment in the reactor/mixer device. In particular, embodiments of the systems and methods may be used in the production of alcohols from the hydroxylation of olefenic alcohols. Preferably, the method comprises a homogeneous phase reaction of liquid olefenic alcohol with a peroxide. The high shear device reduces the mass transfer limitations on the reaction and thus increases the overall reaction rate.

Chemical reactions involving liquids, gases and solids rely on time, temperature, and pressure to define the rate of reactions. In cases where it is desirable to react two or more raw materials of different phases (e.g., solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants. Contact time for the reactants and/or catalyst is often controlled by mixing which provides contact with two or more reactants involved in a chemical reaction. A reactor assembly that comprises an external high shear mixing device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes.

System for Hydroxylation of Olefenic Alcohols.

Figure 1:
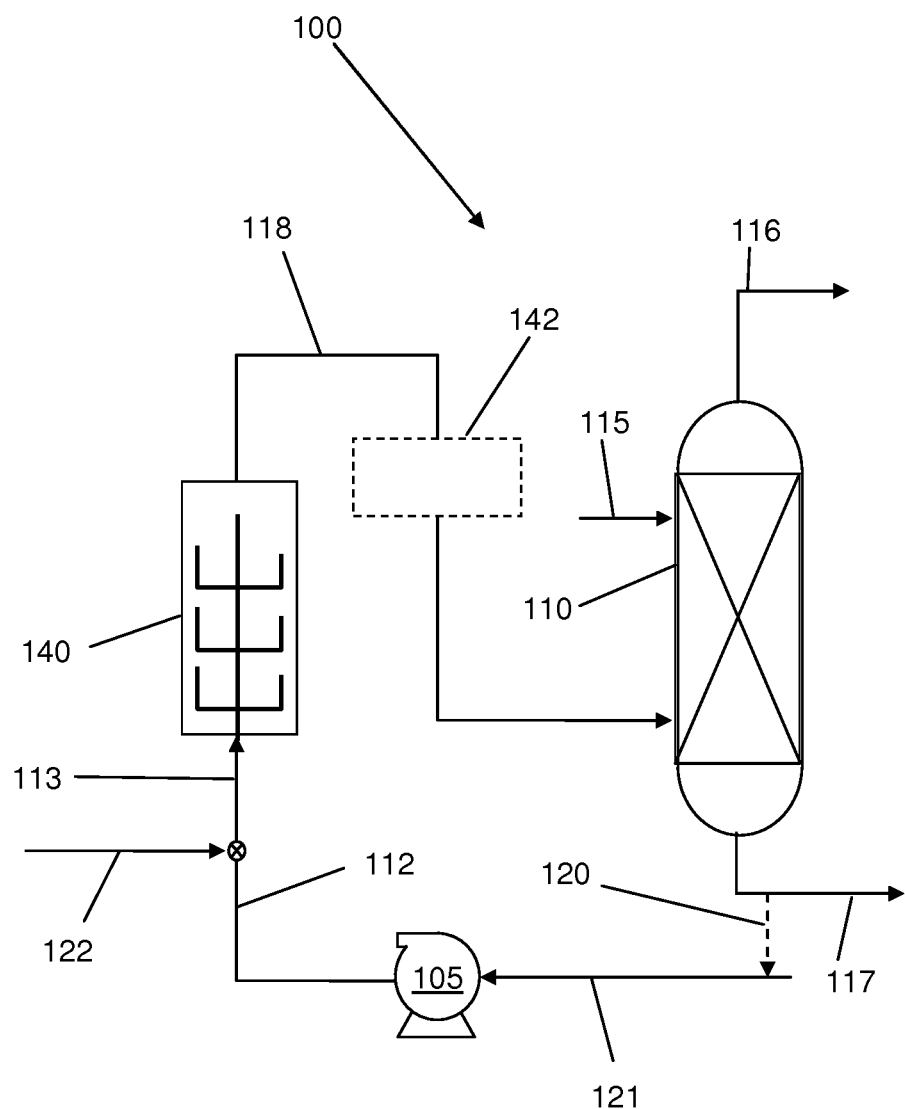
FIG. 1 is a process flow diagram of a process for making glycerol, according to certain embodiments of the invention.

A high shear hydroxylation system will now be described in relation to FIG. 1, which is a process flow diagram of an embodiment of a high shear system 100 for the production of glycerol via the hydroxylation of olefenic alcohols. The basic components of a representative system include external high shear device (HSD) 140, vessel 110, and pump 105. As shown in FIG. 1, the high shear device may be located external to vessel/reactor 110. Each of these components is further described in more detail below. Line 121 is connected to pump 105 for introducing an olefenic alcohol reactant. Line 113 connects pump 105 to HSD 140, and line 118 connects HSD 140 to vessel 110. Line 122 is connected to line 13 for introducing a peroxide stream with the olefenic alcohol stream. Line 117 is connected to vessel 110 for removal of unreacted olefenic alcohol, peroxides, and other reactants. Additional components or process steps may be incorporated between vessel 110 and HSD 140, or ahead of pump 105 or HSD 140, if desired. High shear devices (HSD) such as a high shear mixing device, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 microns. High shear mechanical devices include homogenizers as well as colloid mills.]

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 μm to about 1 μm. At the other end of the spectrum are high shear device systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy-high shear devices and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 μm to about 25 μm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear mixing device is greater than 1000 W/m$^3$. In embodiments, the energy expenditure is in the range of from about 3000 W/m$^3$ to about 7500 W/m$^3$. The shear rate generated in a high shear mixing device may be greater than 20,000 s$^{-1}$. In embodiments, the shear rate generated is in the range of from 20,000 s$^{-1}$ to 100,000 s$^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec) =π·D·n, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, 2πR, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear mixing device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi).

Referring now to FIG. 1, there is presented a schematic diagram of a high shear mixing device 200. High shear mixing device 200 comprises at least one rotor-stator combination. The rotor-stator combinations may also be known as generators 220, 230, 240 or stages without limitation. The high shear mixing device 200 comprises at least two generators, and most preferably, the high shear mixing device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear mixing device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear mixing device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. The rotor and the stator may be of any suitable size. In one embodiment, the inner diameter of the rotor is about 64 mm and the outer diameter of the stator is about 60 mm. In other embodiments, the inner diameter of the rotor is about 11.8 cm and the outer diameter of the stator is about 15.4 cm. In further embodiments, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear mixing device 200, the appropriate gap width is first selected for an appropriate reduction in particle size and increase in particle surface area. In embodiments, this is beneficial for increasing catalyst surface area by shearing and dispersing the particles.

High shear mixing device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear mixing device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the average bubble size is in the range from about 1.0 µm to about 0.1 µm. Alternatively, the average bubble size is less than about 400 nm (0.4 µm) and most preferably less than about 100 nm (0.1 µm).

The high shear mixing device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear mixing device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear mixing device 200 such that the velocity of the reaction is increased by at least about 5%. Alternatively, the high shear mixing device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear mixing device 200 is dependent on throughput requirements and desired particle or bubble size in the outlet dispersion 210. In certain instances, high shear mixing device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min) Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear mixing device resulting in increased temperatures and pressures with the most significant increase believed to be in localized pressures. The increase in pressures and temperatures within the high shear mixing device are instantaneous and localized and quickly revert back to bulk or average system conditions once exiting the high shear mixing device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming).

Vessel.

Vessel or reactor 110 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 110 may be a tower reactor, and in others a tubular reactor or multi-tubular reactor. A catalyst inlet line 115 may be connected to vessel 110 for receiving a catalyst solution or slurry during operation of the system.

Vessel 110 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 140 in some embodiments, vessel 110 may serve primarily as a storage vessel in some cases. Although generally less desired, in some applications vessel 110 may be omitted, particularly if multiple high shear devices/reactors are employed in series, as further described below.

Heat Transfer Devices.

In addition to the above-mentioned heating/cooling capabilities of vessel 110, other external or internal heat transfer devices for heating or cooling a process stream are also contemplated in variations of the embodiments illustrated in FIG. 1. Some suitable locations for one or more such heat transfer devices are between pump 105 and HSD 140, between HSD 140 and vessel 110, and between vessel 110 and pump 105 when system 100 is operated in multi-pass mode. Some non-limiting examples of such heat transfer devices are shell, tube, plate, and coil heat exchangers, as are known in the art.

Pumps.

Pump 105 is configured for either continuous or semi-continuous operation, and may be any suitable pumping device that is capable of providing greater than 2 atm pressure, preferably greater than 3 atm pressure, to allow controlled flow through HSD 140 and system 100. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of the pump comprise stainless steel. In some embodiments of the system, pump 105 is capable of pressures greater than about 20 atm. In addition to pump 105, one or more additional, high pressure pump (not shown) may be included in the system illustrated in FIG. 1. For example, a booster pump, which may be similar to pump 105, may be included between HSD 140 and vessel 110 for boosting the pressure into vessel 110. As another example, a supplemental feed pump, which may be similar to pump 105, may be included for introducing additional reactants or catalyst into vessel 110.

Production of Glycerol.

In operation for the hydroxylation of olefinic alcohols for the production of glycerol, respectively, the olefinic alcohol stream is introduced into system 100 via line 122, and combined in line 113 with a peroxide stream to form a reactant stream. The peroxide may be any suitable peroxide compounds as will be described in more detail below. Alternatively, the peroxide stream may be fed directly into HSD 140, instead of being combined with the liquid reactant (i.e., olefinic alcohol, peroxide) in line 113. Pump 105 is operated to pump the liquid reactants (olefinic alcohol, peroxide) through line 121, and to build pressure and feed HSD 140, providing a controlled flow throughout high shear device (HSD) 140 and high shear system 100.

In a preferred embodiment, peroxide may continuously be fed into the olefinic alcohol stream 112 to form high shear device feed stream 113 (e.g. reactant stream). In high shear device 140, olefinic alcohol and a peroxide are highly sheared such that nanobubbles and/or microbubbles are formed for superior dissolution of peroxide and the alcohol into solution. Once mixed, the reactants may exit high shear device 140 at high shear device outlet line 118. Stream 118 may optionally enter fluidized or fixed bed 142 in lieu of a slurry catalyst process. However, in a slurry catalyst embodiment, high shear outlet stream 118 may directly enter hydroxylation reactor 110 for hydroxylation. The reaction stream may be maintained at the specified reaction temperature, using cooling coils in the reactor 110 to maintain reaction temperature. Hydroxylation products (e.g. glycerol and/or polyols) may be withdrawn at product stream 116.

Figure 2:
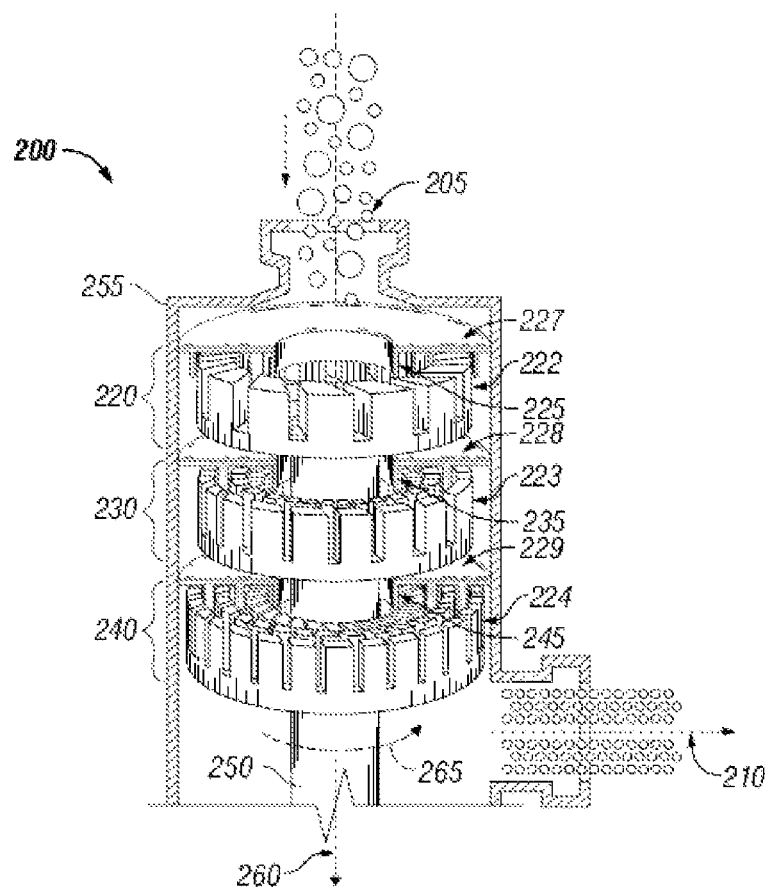
FIG. 2 is a longitudinal cross-section view of a multi-stage high shear mixing device, as employed in an embodiment of the system of FIG. 1.

In an exemplary embodiment, the high shear device comprises a commercial disperser such as IKA® model DR 2000/4, a high shear, three stage dispersing device configured with three rotors in combination with stators, aligned in series. The disperser is used to create reaction solution in the liquid medium comprising the reactants. The rotor/stator sets may be configured as illustrated in FIG. 2, for example. The combined reactants enter the high shear device via line 113 and enter a first stage rotor/stator combination having circumferentially spaced first stage shear openings. The coarse dispersion exiting the first stage enters the second rotor/stator stage, which has second stage shear openings. The reduced bubble-size dispersion emerging from the second stage enters the third stage rotor/stator combination having third stage shear openings. The dispersion exits the high shear device via line 118. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear device includes a PTFE seal, for example, the seal may be cooled using any suitable technique that is known in the art. For example, the reactant stream flowing in line 113 may be used to cool the seal and in so doing be preheated as desired prior to entering the high shear device.

The rotor of HSD 140 is set to rotate at a speed commensurate with the diameter of the rotor and the desired tip speed. As described above, the high shear device (e.g., colloid mill) has either a fixed clearance between the stator and rotor or has adjustable clearance. HSD 140 serves to intimately mix the peroxide and the reactant liquid (i.e., olefenic alcohol). In some embodiments of the process, the transport resistance of the reactants is reduced by operation of the high shear device such that the velocity of the reaction (e.g. reaction rate) is increased by greater than a factor of about 5. In some embodiments, the velocity of the reaction is increased by at least a factor of 10. In some embodiments, the velocity is increased by a factor in the range of about 10 to about 100 fold. In some embodiments, HSD 140 delivers at least 300 L/h with a power consumption of 1.5 kW at a nominal tip speed of at least 4500 ft/min, and which may exceed 7900 ft/min (140 m/sec). Although measurement of instantaneous temperature and pressure at the tip of a rotating shear unit or revolving element in HSD 140 is difficult, it is estimated that the localized temperature seen by the intimately mixed reactants may be in excess of 500° C. and at pressures in excess of 500 kg/cm$^2$ under high shear conditions. The high shear mixing results in formation of micron or submicron-sized bubbles, which may be due to cavitation. In some embodiments, the resultant dispersion has an average bubble size less than about 1.5 μm. Accordingly, the reactant stream exiting HSD 140 via line 118 comprises micron and/or submicron-sized gas bubbles. In some embodiments, the mean bubble size is in the range of about 0.4 μm to about 1.5 μm. In some embodiments, the mean bubble size is less than about 400 nm, and may be about 100 nm in some cases. In many embodiments, the microbubble dispersion is able to remain dispersed at atmospheric pressure for at least 15 minutes.

Once sheared, the resulting reactant solution exits HSD 140 via line 118 and feeds into vessel 110, as illustrated in FIG. 1. As a result of the intimate mixing of the reactants prior to entering vessel 110, a significant portion of the chemical reaction may take place in HSD 140, with or without the presence of a catalyst. Accordingly, in some embodiments, reactor/vessel 110 may be used primarily for heating and separation of volatile reaction products from the alcohol product. Alternatively, or additionally, vessel 110 may serve as a primary reaction vessel where most of the glycerol product is produced. Vessel/reactor 110 may be operated in either continuous or semi-continuous flow mode, or it may be operated in batch mode. The contents of vessel 110 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously. In some embodiments, more than one vessel 110 may be used to hydroxylate the olefenic alcohol. That is, the system 100 may comprise more than one reactor stage.

Commonly known hydroxylation reaction conditions may suitably be employed as the conditions of the production of an alcohol by hydroxylating an olefenic alcohol by using the catalysts. There is no particular restriction as to the reaction conditions. However, the pressure is selected usually within a range of from about atmospheric pressure to 100 atm, more preferably from 10 to 60 atm, and the reaction temperature may be within a range of from about 5° C. to about 100° C., alternatively from about 20° C. to about 80° C., alternatively from about 40° C. to about 60° C.

As mentioned above, any suitable unsaturated or olefenic alcohols may be hydroxylated in conjunction with the disclosed methods and processes. As used herein, an olefenic alcohol is any compound containing at least a double bond and a primary hydroxyl group. The olefenic alcohol may be branched, linear, or cyclic in structure. Examples of such alcohols include without limitation, allyl alcohol, methallyl alcohol, cinnamyl alcohol, methyl vinyl carbinol, dimethyl allyl alcohol, oleyl alcohol, methyl vinyl carbinol, crotyl alcohol, methyallyl alcohol, cyclohexenol, and the like.

The oxidant for the hydroxylation reaction may at least one organic hydroperoxide. Conventional organohydroperoxides include those having the formula: ROOH, where R may be hydrogen or a substituted or unsubstituted: alkyl, typically about $C_3$ to about $C_{20}$, preferably about $C_3$ to about $C_{10}$, most preferably about $C_3$ to about $C_6$ alkyl; aryl, typically $C_6$ to $C_{14}$, preferably $C_6$ to C.sub.10, most preferably $C_6$ aryl; aralkyl and alkaryl wherein the aryl and alkyl groups thereof are as defined immediately above; cycloalkyl, typically about $C_4$ to about $C_{20}$, preferably about $C_4$ to about $C_{10}$, most preferably about $C_4$ to about $C_8$ cycloalkyl; as well as oxacyclic having 1 to about 5 oxygens and preferably 3 to about 20 carbons, and azacyclic having 1 to about 5 nitrogens and preferably about 3 to about 20 carbons; and wherein the substituents of said R group include halogen, hydroxyl, ester and ether groups.

Representative examples of suitable organohydroperoxides include ethylbenzyl hydroperoxide, t-butyl hydroperoxide, t-amyl hydroperoxide, cumene hydroperoxide, 2-methyl-2-hydroperoxy-methyl proprionate, 2-methyl-2-hydroperoxy propanoic acid, pyrrolehydroperoxide, furan hydroperoxide, 2-butylhydroperoxide, cyclohexyl hydroperoxide, and 1-phenyl-ethylhydroperoxide.

Catalyst.

If a catalyst is used to promote the hydroxylation reaction, it may be introduced into the vessel via line 115, as an aqueous or nonaqueous slurry or stream. Alternatively, or additionally, catalyst may be added elsewhere in the system 100. For example, catalyst slurry may be injected into line 121. In some embodiments, line 121 may contain a flowing recycle stream containing peroxide and/or olefenic alcohol from vessel 110.

In embodiments, any catalyst suitable for catalyzing a hydroxylation reaction may be employed. Suitable catalysts may be any of the catalysts normally used for hydroxylation of olefins. The catalysts may comprise transition metals such as without limitation, transition metals such as zirconium, vanadium, niobium, tantalum, chromium, molybdenum, tungsten, rhenium and uranium. Examples of suitable catalysts include without limitation, a metal oxide such as tungsten oxide or molybdenum oxide, a tungstic catalyst, osmium catalysts, formic acid, sulfonic acid, sulfuric acid, or combinations thereof. Further examples of suitable catalysts include without limitation, selenotungstic acid, sulfotungstic acid, molybdotungstic acid, tungstic acid, molybdenum naphthenate, molybdenum hexacarbonyl, phosphomolybdic acid, molybdenum trioxide, titanium naphthenate, tungsten carbonyl, rhenium heptoxide, columbium naphthenate, tetrabutyl titanate, a mixture of molybdenum naphthenate and sodium naphthenate, tungstic oxide, sodium tungstate.

The bulk or global operating temperature of the reactants is desirably maintained below their flash points. In some embodiments, the operating conditions of system 100 comprise a temperature in the range of from about 10° C. to about 300° C. In specific embodiments, the reaction temperature in vessel 110, in particular, is in the range of from about 20° C. to about 100° C. In some embodiments, the reaction pressure in vessel 110 is in the range of from about 1 atm to about 50 atm.

The reactant stream may be further processed prior to entering vessel 110 (as indicated by arrow 18), if desired. In vessel 110, olefenic alcohol hydroxylation occurs via catalytic hydroxylation. The contents of the vessel are stirred continuously or semi-continuously, the temperature of the reactants is controlled (e.g., using a heat exchanger), and the fluid level inside vessel 110 is regulated using standard techniques. Olefenic alcohol hydroxylation may occur either continuously, semi-continuously or batch wise, as desired for a particular application. Any by-products that are produced may exit reactor 110 via line 117. This stream may comprise unreacted alcohol, and peroxides, for example. The unconverted reactants and/or byproducts removed via line 117 may be further treated, and the components may be recycled, as desired. In a specific embodiment, unconverted olefenic alcohol from vessel 110 may be recycled back to line 121 through line 120.

The reaction product stream including unconverted peroxide and/or olefenic alcohol and corresponding byproducts exits vessel 110 by way of line 116. The glycerol product may be recovered and treated as known to those of skill in the art.

Multiple Pass Operation.

In the embodiment shown in FIG. 1, the system is configured for single pass operation, wherein the output from vessel 110 goes directly to further processing for recovery of alcohol product. In some embodiments it may be desirable to pass the contents of vessel 110, or a liquid fraction containing unreacted olefenic alcohol, through HSD 140 during a second pass. In this case, line 117 is connected to line 121 via dotted line 120, and the recycle stream from vessel 110 is pumped by pump 105 into line 113 and thence into HSD 140. Additional peroxide stream may be injected via line 122 into line 113, or it may be added directly into the high shear device (not shown).

Multiple High Shear Mixing Devices.

In some embodiments, two or more high shear devices like HSD 140, or configured differently, are aligned in series, and are used to further enhance the reaction. Their operation may be in either batch or continuous mode. In some instances in which a single pass or "once through" process is desired, the use of multiple high shear mixing devices in series may also be advantageous. In some embodiments where multiple high shear mixing devices are operated in series, vessel 110 may be omitted. In some embodiments, multiple high shear mixing devices 140 are operated in parallel, and the outlet dispersions therefrom are introduced into one or more vessel 110.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of producing glycerol comprising:

mixing a peroxide stream with an olefinic alcohol stream to form a feed stream;

processing the feed stream in a high shear device to produce a dispersion of peroxide and olefinic alcohol, wherein the dispersion comprises bubbles with an average bubble diameter of less than about 5 microns, and wherein the high shear device is configured with a rotor and a stator separated by a shear gap; and contacting the dispersion with a catalyst in a reactor to produce glycerol, wherein the reactor operates at a bulk reaction pressure of about 10 to about 60 atm.

2. A method of producing glycerol comprising:

mixing a peroxide stream with an olefinic alcohol stream to form a feed stream;

processing the feed stream in a high shear device to produce a dispersion of peroxide and olefinic alcohol, wherein the high shear device is configured with a rotor and a stator separated by a shear gap, wherein the high shear device operates at a tip speed of at least about 23 m/sec, and subjects the feed stream to a shear rate of greater than about 20,000 $s^{-1}$; and contacting the dispersion with a catalyst in a reactor to produce glycerol, wherein the reactor operates at a bulk reaction pressure of about 10 to about 60 atm.

3. A method of producing glycerol comprising:

mixing a peroxide stream with an olefinic alcohol stream to form a feed stream;

processing the feed stream in a high shear device to produce a dispersion of peroxide and olefinic alcohol, wherein the high shear device is configured with a rotor and a stator separated by a shear gap, wherein forming the dispersion comprises operating the high shear device at an energy expenditure of at least about 1000 W/m$^3$, and wherein the shear gap is in the range of from about 0.02 mm to about 5 mm; and contacting the dispersion with a catalyst in a reactor to produce glycerol, wherein the reactor operates at a bulk reaction pressure of about 10 to about 60 atm.

4. The method of claim 3, further comprising introducing the dispersion to a fixed bed containing additional catalyst.

5. A method of producing glycerol comprising:

mixing a peroxide stream with an olefenic alcohol stream to form a reactant stream;

processing the reactant stream in a high shear device to produce a dispersion comprising peroxide and olefinic alcohol, wherein the high shear device is configured with a rotor and a stator separated by a shear gap; and contacting the high shear dispersion with a catalyst in a reactor to produce glycerol, wherein the reactor operates at a bulk reaction pressure of about 10 to about 60 atm, and a bulk reaction temperature of about 20° C. to about 80° C.

6. The method of claim 5, wherein the dispersion comprises bubbles having an average bubble size less than about 1.5 μm.

7. The method of claim 5, wherein the dispersion comprises bubbles with an average diameter of less than about 5 microns.

8. The method of claim 7, wherein the peroxide stream comprises hydrogen peroxide, ethylbenzyl hydroperoxide, t-butyl hydroperoxide, t-amyl hydroperoxide, cumene hydroperoxide, 2-methyl-2-hydroperoxy-methyl proprionate, 2-methyl-2-hydroperoxy propanoic acid, pyrrolehydroperoxide, furan hydroperoxide, 2-butylhydroperoxide, cyclohexyl hydroperoxide, and 1-phenyl-ethylhydroperoxide, or combination thereof.

9. The method of claim 8, wherein the olefenic alcohol stream comprises allyl alcohol, methallyl alcohol, cinnamyl alcohol, methyl vinyl carbinol, dimethyl allyl alcohol, oleyl alcohol, methyl vinyl carbinol, crotyl alcohol, methyallyl alcohol, cyclohexenol, or combinations thereof.

10. The method of claim 5, wherein the high shear device operates at a tip speed of at least about 23 m/sec, and subjects the feed stream to a shear rate of greater than about 20,000 $s^{-1}$.

11. The method of claim 10, wherein forming said dispersion comprises operating the high shear device at an energy expenditure of at least about 1000 W/m$^3$, and wherein the shear gap is in the range of from about 0.02 mm to about 5 mm.

12. The method of claim 5, wherein the catalyst comprises a metal oxide, a tungstic catalyst, an osmium catalyst, formic acid, sulfonic acid, sulfuric acid, or combinations thereof.

13. The method of claim 5, wherein the shear gap is in the range of from about 0.02 mm to about 5 mm, and wherein the high shear device produces a tip speed of the rotor of greater than about 23 m/s (4,500 ft/min).

* * * * *